US007869571B2

(12) United States Patent
Hsieh et al.

(10) Patent No.: US 7,869,571 B2
(45) Date of Patent: Jan. 11, 2011

(54) METHODS AND APPARATUS FOR X-RAY IMAGING WITH FOCAL SPOT DEFLECTION

(75) Inventors: Jiang Hsieh, Brookfield, WI (US); Eugne Lino Saragnese, Delafield, WI (US); J. Eric Stahre, Oconomowoc, WI (US); Bijan Dorri, Waukesha, WI (US); James Kaufman, Milwaukee, WI (US); Robert Franklin Senzig, Germantown, WI (US)

(73) Assignee: General Electric Company, Schenectady, NY (US)

( * ) Notice: Subject to any disclaimer, the term of this patent is extended or adjusted under 35 U.S.C. 154(b) by 63 days.

(21) Appl. No.: 12/324,348

(22) Filed: Nov. 26, 2008

(65) Prior Publication Data

US 2010/0067651 A1 Mar. 18, 2010

Related U.S. Application Data

(60) Provisional application No. 61/097,808, filed on Sep. 17, 2008.

(51) Int. Cl.
*H01J 35/08* (2006.01)
*H01J 35/10* (2006.01)
*H05G 1/60* (2006.01)

(52) U.S. Cl. ............................ 378/124; 378/144; 378/4

(58) Field of Classification Search ..................... 378/4, 378/11, 19, 143, 144, 124, 17, 125
See application file for complete search history.

(56) References Cited

U.S. PATENT DOCUMENTS

| | | | | |
|---|---|---|---|---|
| 5,469,429 | A | 11/1995 | Yamazaki et al. | |
| 5,550,889 | A | 8/1996 | Gard et al. | |
| 6,111,934 | A | 8/2000 | Foerst et al. | |
| 6,438,207 | B1 | 8/2002 | Chidester et al. | |
| 6,483,890 | B1 | 11/2002 | Malamud | |
| 6,973,158 | B2 | 12/2005 | Besson | |
| 6,983,035 | B2 * | 1/2006 | Price et al. | 378/124 |
| 7,012,989 | B2 * | 3/2006 | Holland et al. | 378/144 |
| 7,042,975 | B2 * | 5/2006 | Heuscher | 378/8 |
| 7,305,063 | B2 * | 12/2007 | Heuscher | 378/12 |
| 7,406,154 | B2 | 7/2008 | Resnick | |
| 2004/0264626 | A1 | 12/2004 | Besson | |
| 2004/0264628 | A1 | 12/2004 | Besson | |
| 2006/0115050 | A1 | 6/2006 | Resnick | |
| 2008/0247504 | A1 | 10/2008 | Edic et al. | |
| 2008/0285716 | A1 | 11/2008 | Tang et al. | |
| 2009/0185656 | A1 * | 7/2009 | Heuscher | 378/11 |

* cited by examiner

*Primary Examiner*—Irakli Kiknadze
(74) *Attorney, Agent, or Firm*—Dean Small; Small Patent Law Group

(57) ABSTRACT

Methods and apparatus for x-ray imaging with focal spot deflection are provided. The apparatus includes an x-ray tube having a cathode configured to emit electrons and an anode having a target with a target surface defining a target angle. The emitted electrons are deflected onto the target surface with the target surface substantially aligned with a z-axis parallel to a gantry rotation axis.

30 Claims, 7 Drawing Sheets

METHODS AND APPARATUS FOR X-RAY IMAGING WITH FOCAL SPOT DEFLECTION

CROSS REFERENCE TO RELATED APPLICATIONS

This application claims priority to and the benefit of the filing date of U.S. Provisional Application No. 61/097,808, filed Sep. 17, 2008 for "METHODS AND APPARATUS FOR X-RAY IMAGING WITH FOCAL SPOT DEFLECTION," which is hereby incorporated by reference herein in its entirety.

BACKGROUND OF THE INVENTION

This invention relates generally to imaging methods and apparatus, and more particularly to methods and apparatus for imaging using x-ray tubes.

In computed tomography (CT) imaging systems, such as a CT imaging system performing cone beam imaging in a step-and-shoot mode of data acquisition, projection sampling is incomplete. There are two major sources of the incomplete sampling, which are the cone beam effect and longitudinal truncation. In particular, other than the center plane, exact reconstruction is not possible, which is the cone beam effect. Although many approximation algorithms are known to compensate for the cone beam effect, image artifacts become clinically unacceptable when the cone beam becomes large, such as when imaging larger regions (e.g., using a large image detector for an entire organ). Longitudinal truncation results because the coverage along the gantry rotation axis changes as a distance to the x-ray focal spot. Specifically, the coverage is much smaller for regions closer to the focal spot. As a result, a portion of the imaging volume to be reconstructed is not exposed to the x-ray radiation.

To overcome the cone beam and longitudinal truncation artifacts in, for example, a step-and-shoot mode CT, systems with multiple x-ray focal spots are known. Using two focal spot spaced along the z-direction (longitudinal direction of scanning) can significantly reduce the cone beam and truncation artifacts. Thus, it is desirable to provide an x-ray tube that produces two focal spots in the z-direction during data acquisition. During scanning, the two focal spots can be switched on and off alternatively such that each voxel in the reconstructed volume is irradiated from two different cone angles while at substantially the same projection view angle.

BRIEF DESCRIPTION OF THE INVENTION

In one aspect, some embodiments of the present invention provide an x-ray tube including a cathode configured to emit electrons and an anode having a target with a target surface defining a target angle. The emitted electrons are deflected onto the target surface with the target surface substantially aligned with a z-axis parallel to a gantry rotation axis.

In another aspect, some embodiments of the present invention provide a computed tomography (CT) system that includes a gantry having a gantry opening therethrough defining a z-axis. The gantry is configured to rotate about the z-axis. The CT system further includes a radiation source coupled to the gantry. The radiation source utilizes focal spot deflection to project x-rays into the gantry opening and the radiation source is offset from the z-axis.

In yet another aspect, some embodiments of the present invention provide a method for generating x-ray beams with an x-ray tube. The method includes generating a plurality of deflected focal spots along a target of the x-ray tube and aligning an angled surface of the target with a z-axis along which x-ray beams generated by the deflected focal spots are projected.

DETAILED DESCRIPTION OF THE INVENTION

Figure 1:
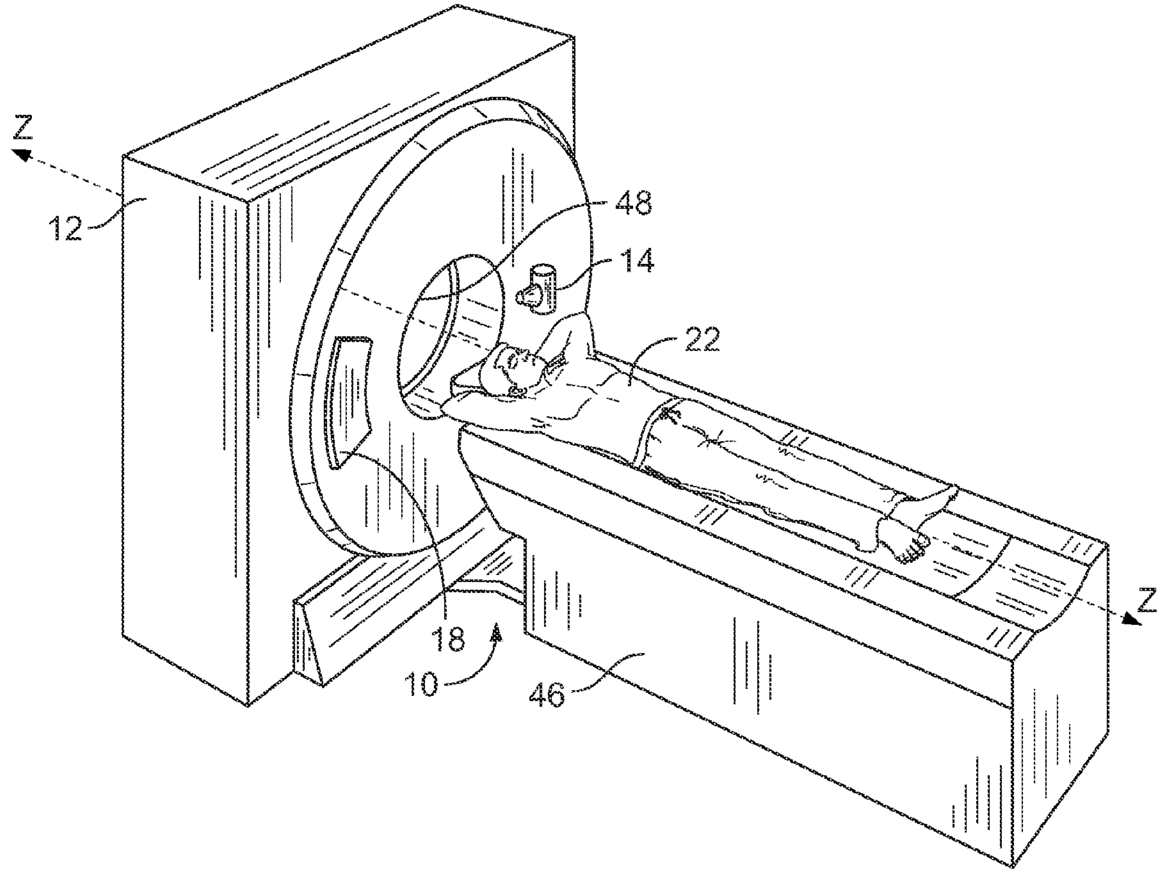
FIG. 1 is a perspective view of a computed tomography (CT) imaging system constructed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings, nor are the figures necessarily drawn to scale.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Additionally, the recitation of a particular number of elements does not exclude embodiments having more than that particular number, unless the number is further qualified by words such as "exactly" or "only." Also, unless the possibility is either explicitly, logically, or physically excluded, individual features may be omitted from an embodiment, or one or more features from another embodiment or other embodiments, may be combined to produce additional embodiments of the present invention.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Various embodiments may be implemented in connection with different types of imaging systems. For example, various embodiments may be implemented in connection with a CT imaging system in which an x-ray source using focal spot deflection (multiple focal spots may be provided) projects a fan-shaped beam that is collimated to lie within an X-Y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. In an axial scan (e.g., a step-and-shoot axial scan), the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, a patient or object (e.g., baggage) is moved while the data for a prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighting algorithms that weight the acquired data as a function of view angle and detector channel index. Specifically, prior to a filtered backprojection process, the data is weighted according to a helical weighing factor, which is a function of both the gantry angle and the detector angle. The weighted data is then processed to generate CT numbers and to construct an image that corresponds to a two-dimensional slice taken through the object.

Technical effects of embodiments of the present invention include providing increased focal spot spacing with less focal spot deflection. Also, heat generated by an x-ray tube is distributed over a larger track surface to allow higher total x-ray flux. The manner in which these and other technical effects of embodiments of the present invention are achieved will become apparent to one of ordinary skill in the art upon based on the subject matter described herein.

Figure 2:
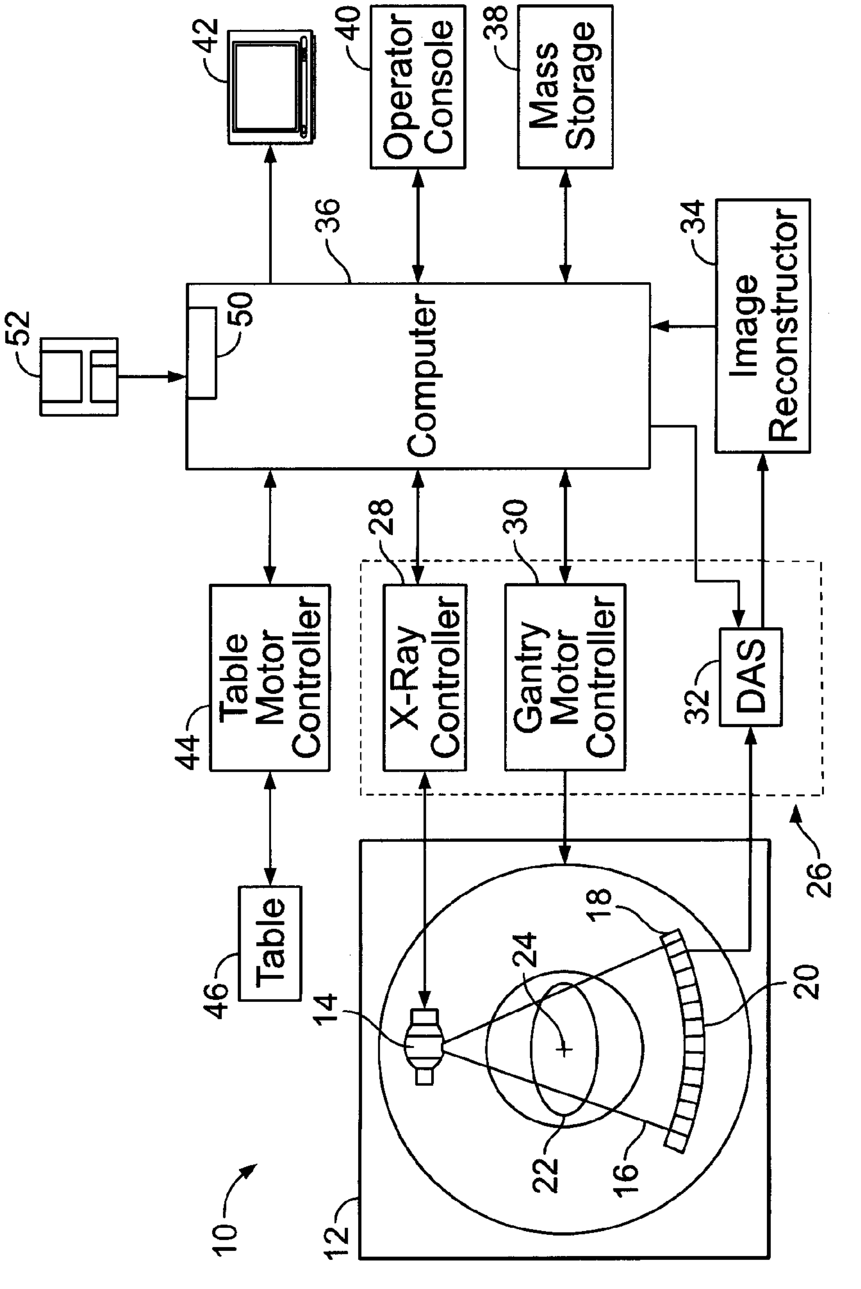
FIG. 2 is a block diagram of a CT imaging system constructed in accordance with various embodiments of the invention.

FIG. 1 is a pictorial view of a CT imaging system 10 formed in accordance with various embodiments of the invention. FIG. 2 is a block schematic diagram of the CT imaging system 10 illustrated in FIG. 1. In the exemplary embodiment, a computed tomography (CT) imaging system 10 is shown as including a gantry 12 representative of a "third generation" CT imaging system. The gantry 12 has a radiation source 14 that projects a cone beam 16 of X-rays toward a detector array 18 on the opposite side of the gantry 12.

The detector array 18 is formed by a plurality of detector rows (not shown) including a plurality of detector elements 20 that together sense the projected X-ray beams that pass through an object, such as a medical patient 22. Each detector element 20 produces an electrical signal that represents the intensity of an impinging radiation beam and hence the attenuation of the beam as the beam passes through object or patient 22. The CT imaging system 10 having a multislice detector 18 is capable of providing a plurality of images representative of a volume of patient 22. Each image of the plurality of images corresponds to a separate "slice" of the volume. The "thickness" or aperture of the slice is dependent upon the thickness of the detector rows.

During a scan to acquire radiation projection data, the gantry 12 and the components mounted thereon rotate about a center of rotation 24 defining a gantry rotation axis (the z-axis or z-direction), illustrated by the dashed line Z in FIG. 1. The z-axis extends into and through the gantry opening 48. In various embodiments, the radiation source 14 includes an x-ray tube that uses focal spot deflection and has a target aligned with the z-axis as described in more detail below.

FIG. 2 shows only a single row of detector elements 20 (i.e., a detector row). However, the multislice detector array 18 includes a plurality of parallel detector rows of detector elements 20 such that projection data corresponding to a plurality of quasi-parallel or parallel slices can be acquired simultaneously during a scan.

Rotation of the gantry 12 and the operation of the radiation source 14 (and optionally movement of the radiation source 14) are governed by a control mechanism 26 of the CT imaging system 10. The control mechanism 26 includes a radiation controller 28 that provides power and timing signals to the radiation source 14 and a gantry motor controller 30 that controls the rotational speed and position of the gantry 12. A data acquisition system (DAS) 32 in the control mechanism 26 samples analog data from the detector elements 20 and converts the data to digital signals for subsequent processing. An image reconstructor 34 receives sampled and digitized radiation data from the DAS 32 and performs high-speed image reconstruction. The reconstructed image is applied as an input to a computer 36 that stores the image in a mass storage device 38.

The computer 36 also receives commands and scanning parameters from an operator via a console 40 that has, for example, a keyboard and/or other user input device(s). An associated display system 42 allows the operator to observe the reconstructed image and other data from the computer 36. The operator supplied commands and parameters are used by the computer 36 to provide control signals and information to the DAS 32, the radiation controller 28 and the gantry motor controller 30. In addition, the computer 36 operates a table motor controller 44 that controls a motorized table 46 to position the patient 22 in the gantry 12 or to move the patient 22 along the z-axis. In particular, the table 46 moves portions of the patient 22 through the gantry opening 48.

In one embodiment, the computer 36 includes a device 50, for example, a floppy disk drive, CD-ROM drive, or DVD-ROM drive, for reading instructions and/or data from a computer-readable medium 52, such as a floppy disk, CD-ROM, or DVD. It should be understood that other types of suitable computer-readable memory are recognized to exist (e.g., CD-RW and flash memory, to name just two), and that this description is not intended to exclude any of these. In another embodiment, the computer 36 executes instructions stored in firmware (not shown). Generally, a processor in at least one of the DAS 32, the reconstructor 34, and the computer 36 shown in FIG. 2 is programmed to execute the processes described below. However, the method is not limited to practice in the CT imaging system 10 and can be utilized in connection with many other types and variations of imaging systems. In one embodiment, the computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
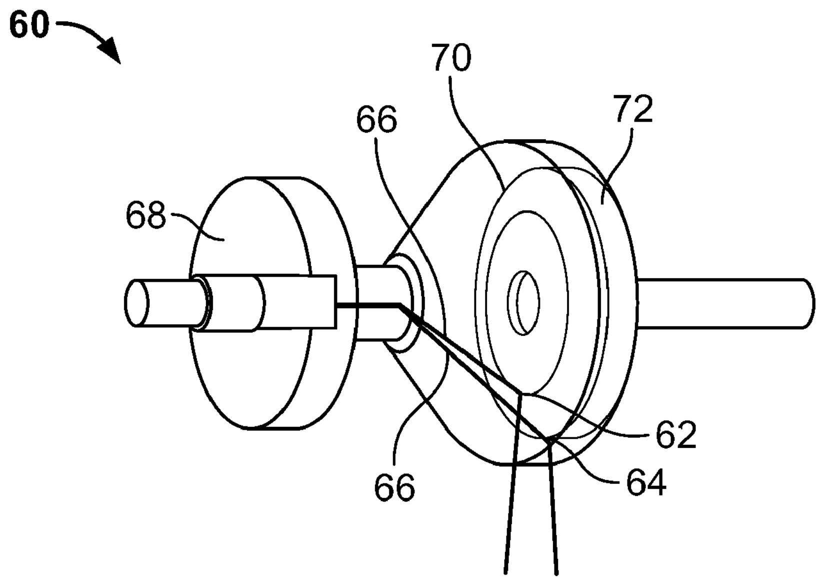
FIG. 3 is a pictorial representation of an x-ray tube that uses focal spot deflection for performing x-ray imaging in accordance with various embodiments of the invention.

Various embodiments of the invention provide an x-ray tube 60 as shown in FIG. 3, which uses focal spot deflection. It should be noted that the various embodiments may be implemented in connection with any type of x-ray tube that can deflect focal spots in the z-direction and are not limited to the x-ray tube illustrated in FIG. 3. Moreover, the focal spot deflection may be provided using any known method, for example, using an electromagnetic field or an electrostatic field generated by an electromagnetic field source or an electrostatic field source, respectively. Other methods of producing multiple focal spots also may be used. For example, multiple focal spots in the z-direction may be produced using nano-tube technology, multiple anodes and cathodes in an x-ray tube, or by placing multiple small x-ray tubes along the z-axis.

The x-ray tube 60 utilizes multiple focal spots 62 and 64 (two focal spots are illustrated) spaced along the target radial direction. A cathode 68 of the x-ray tube 60 generates electron beams 66 that are deflected dynamically in some embodiments using a magnetic field such that the focal spots 62 and 64 are spaced apart on a target 70 of an anode 72 (e.g., a rotating anode). The target 70 may be an annular shaped element on the anode 72. Cooling of the components of the x-ray tube 60 may be provided using any known manner (e.g., liquid cooling system).

Figure 4:
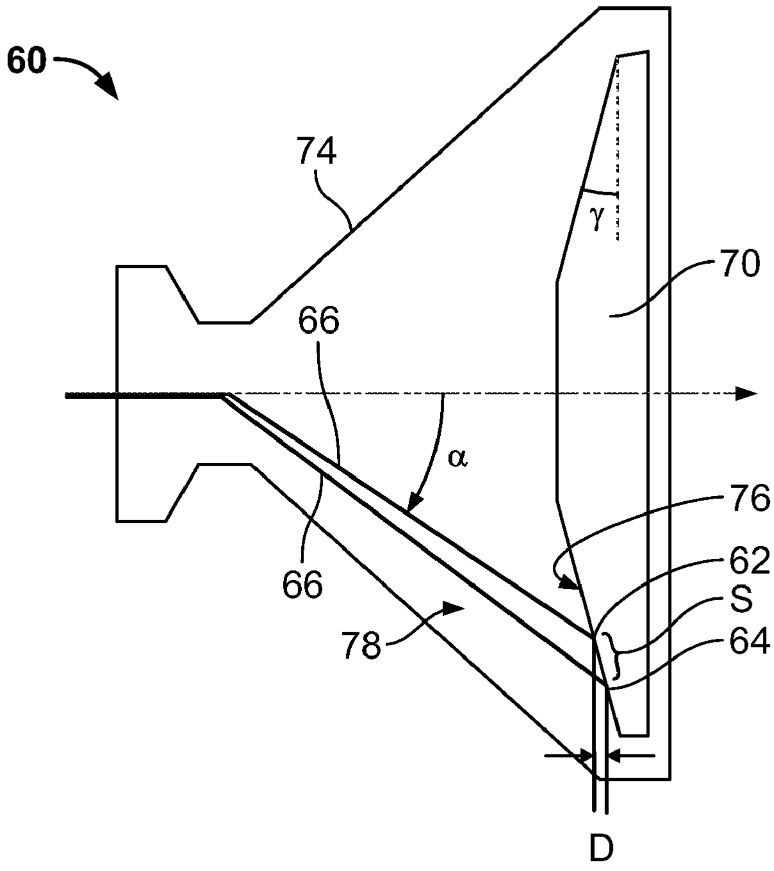
FIG. 4 is a diagram illustrating focal spot deflection in an x-ray tube.

In operation, when the magnetic field changes quickly, the electron beams 66 can be directed at two different locations on the target 70 to produce two distinct focal spots 62 and 64 that may be separated by small distance S in the z-direction as shown in FIG. 4, for example, six millimeters (mm). The components of the x-ray tube 60 in FIG. 4 are shown in a housing 74.

Figure 5:
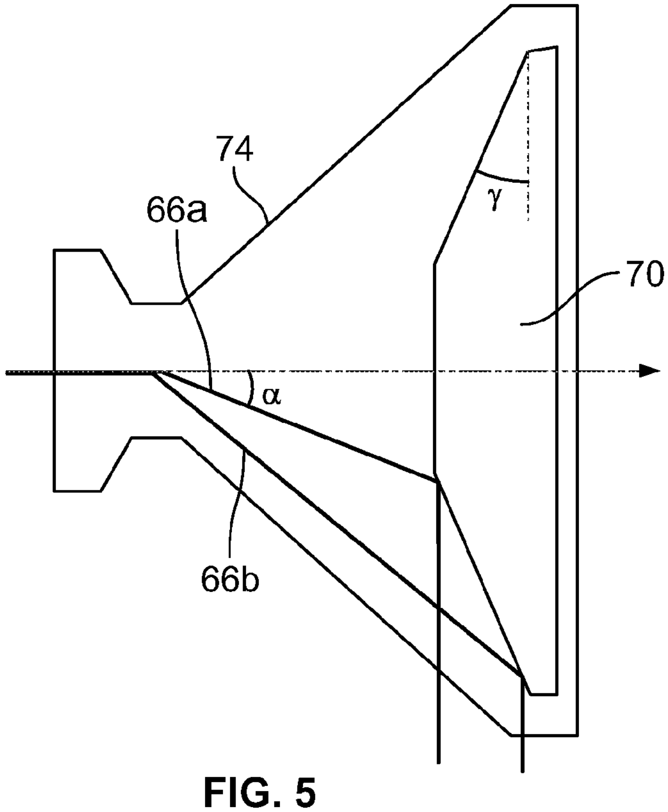
FIG. 5 is a diagram illustrating focal spot deflection in an x-ray tube having an increased focal spot spacing.

In various embodiments, and for example, in order to minimize aliasing artifacts in the z-direction, the spacing between the two focal spots 62 and 64 on the target 70 is provided such that the x-rays connecting one of the focal spots 62 or 64 to the detector cells (e.g., the detector elements 20 shown in FIG. 2) interlace the x-rays connecting the other focal spot 64 or 62 to the detector cells in the z-direction. For illustrative purposes only, and based on a detector-to-iso distance of 408 mm and a projected cell spacing at the iso-center of 0.625 mm, the deflection distance D in the z-direction is 0.73 mm. For a target 70 having a angled portion 76 (e.g., an angled outer surface) with an angle of 7 degrees (i.e., the angle between the target surface and the x-y plane), the distance between the two focal spots 62 and 64 along the target surface 78 is determined as follows: 0.73/sin(7°)=5.96 mm. Accordingly, by changing the amount of the deflection angle $\alpha$ and/or the target angle $\gamma$, the spacing of the focal spots 62 and 64 on the target 70 can be increased even more (e.g., significantly or substantially increased). For example, with a spacing of 50 mm along the target surface 78 as shown in FIG. 5, a difference in the deflection angles between the electron beams 66*a* and 66*b* results in an increased target angle $\gamma$.

Accordingly, use of focal spot deflection and the angled portion 76 provides increased spacing between the two focal spots 62 and 64. For example, if the two focal spots 62 and 64 are separated in the z-direction (referred to as the twin peak concept), cone beam artifacts for a large coverage area are reduced. For illustrative purposes only, for a detector z-coverage of 100 mm at the iso-center, a 80 mm spacing between the two focal spots 62 and 64 can produce images nearly free of cone beam artifacts in the step-and-shoot mode acquisition. It should be noted that that the spacing of the focal spots 62 and 64 along the target surface 78 is magnified by the factor 1/sin($\gamma$) as compared to the spacing of the focal spots 62 and 64 in the z-direction. It also should be noted that when $\gamma$ is less than 45 degrees, the spacing along the target surface 78 is always larger than the spacing along the z-direction.

Figure 6:
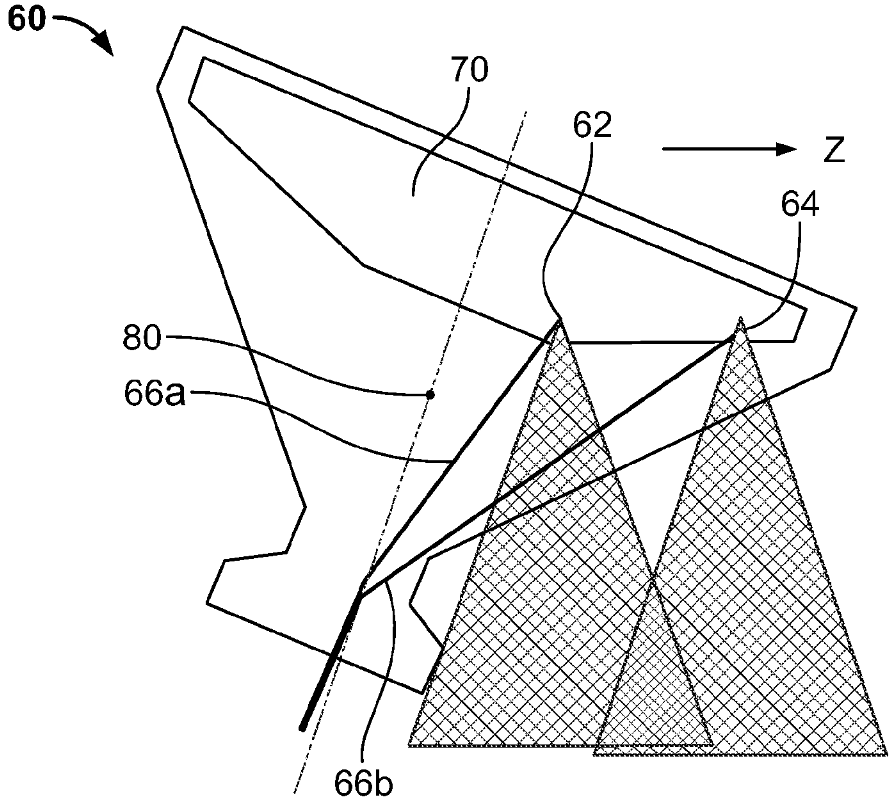
FIG. 6 is a diagram illustrating the target of a focal spot deflected x-ray tube aligned with a z-axis in accordance with various embodiments of the invention.

In various embodiments, and to provide increased spacing between the focal spots, the target surface 78, for example, the angled portion 76 is aligned with the z-axis as shown in FIG. 6. For example, the x-ray tube 60 is offset from the z-axis. For example, the cathode 68 (shown in FIG. 3) that extends along a longitudinal axis of the x-ray tube 60 is offset from the z-axis. In some embodiments, the x-ray tube 60 may be mounted in an offset orientation on the gantry 12 (shown in FIG. 1). For example, the radiation source 14 may be provided in an offset orientation on the gantry 12 such that a target of the radiation source 14 is aligned with the gantry rotation axis or z-axis. It should be noted that the x-ray tube 60 may be mounted in a fixed orientation or may be movable (e.g., pivotally mounted), which movement may be provided manually by hand or mechanically using a motor, which may be provided dynamically. For example, the x-ray tube 60 may be rotated in an axis parallel to the z-axis and about a pivot point 80 as shown in FIG. 6.

Modifications and variations to the various embodiments may be provided. For example, the x-ray tube axis may be tilted with respect to the z-axis so that the amount of tilt is adjusted such that the spacing between a plurality of focal spots can be changed. As another example, the gantry 12 may remain stationary during data acquisition with the plurality of focal spot along the z-axis producing increased coverage for an x-ray radiographic mode of imaging. The mode serves, for example, as a pre-screening for a CT procedure.

As a further example, the x-ray tube 60 may be used in the x-ray radiography mode of the CT imaging system 10. In this mode, the gantry 12 does not rotate with respect to the patient 22. The two focal spots 62 and 64 are turned on sequentially to enable a large coverage of the patient 22 in the z-direction so that an x-ray radiographic image of, for example, the entire organ is obtained. In order to enhance the spatial resolution, the x-ray focal spot can be deflected slighted in the x-direction and z-direction to achieve double sampling. As still a further example, the x-ray tube 60 can be used for tomosynthesis data acquisition in which the gantry 12 remains stationary while the motorized table 46 translates.

Thus, in various embodiments, a tilted tube CT system may be provided and that operates as an x-ray radiography or tomosynthesis device to provide semi-tomographic capability. As a result of the significantly reduced radiation dose compared to a normal CT scan operation, the radiography mode or the tomosynthesis mode can be used, for example, for pre-screening to determine the need for a normal or complete CT scan.

Figure 7:
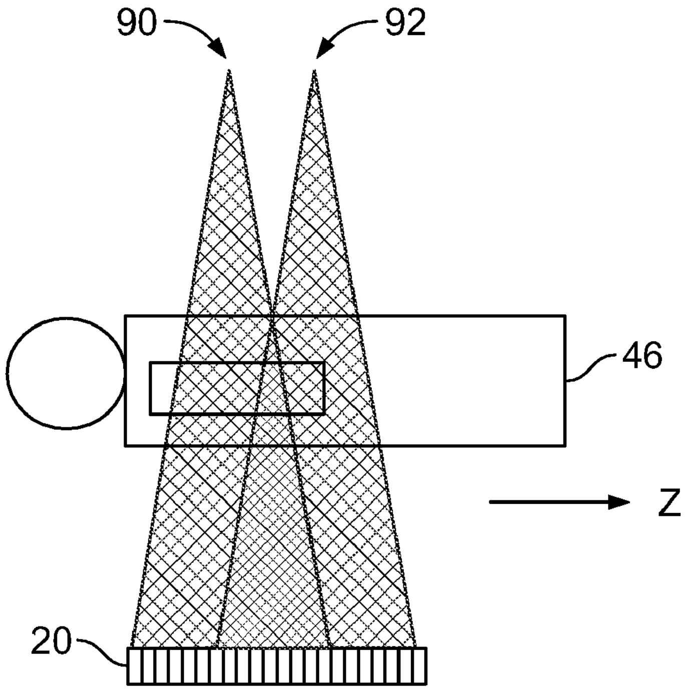
FIG. 7 is a diagram illustrating a radiography mode of operation performed in accordance with various embodiments of the invention.
Figure 8:
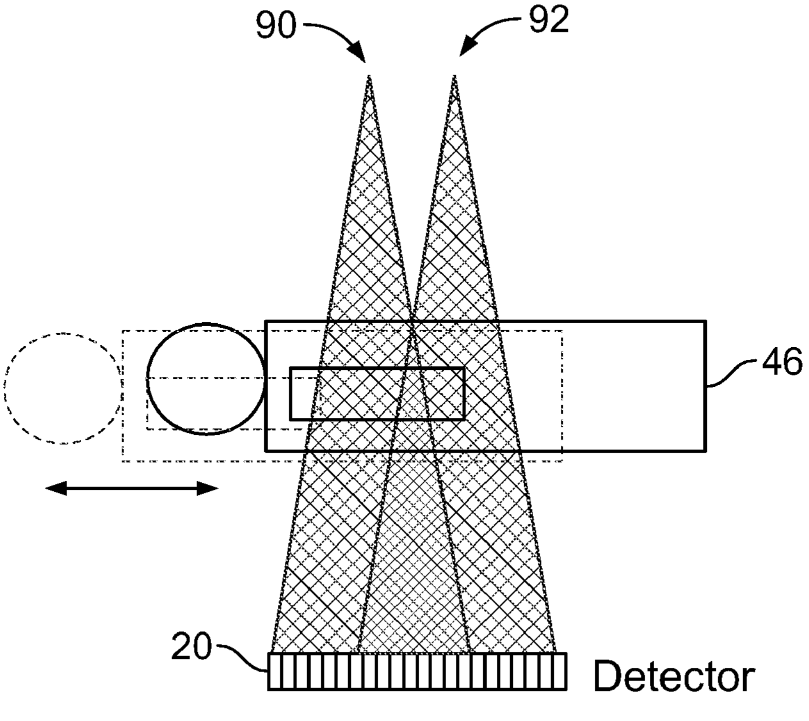
FIG. 8 is a diagram illustrating a tomosynthesis mode of operation performed in accordance with various embodiments of the invention.

In particular, in the radiography mode as illustrated in FIG. 7, both the gantry 12 (shown in FIG. 1) and the motorized table 46 remain stationary. Sequential deflected focal spots 90 and 92 provide increased z-direction coverage. It should be noted that additional focal spot deflection in the x-direction and z-direction can also be used to produce interlaced samples in x and z to enhance spatial resolution. In the tomosynthesis mode as illustrated in FIG. 8, the gantry 12 (shown in FIG. 1) remains stationary, but the motorized table 46 translates along the z-axis. The two focal spots 90 and 92 are turned on sequentially (with deflection) during table translation. Because each point in the scanned object is viewed from several different angles as the motorized table 46 moves (represented by the arrow), a tomosynthesis effect can be produced. Further, using various algorithms known in the art, images can be generated that partially remove the overlapping structures and enable better visualization of the object.

Figure 9:
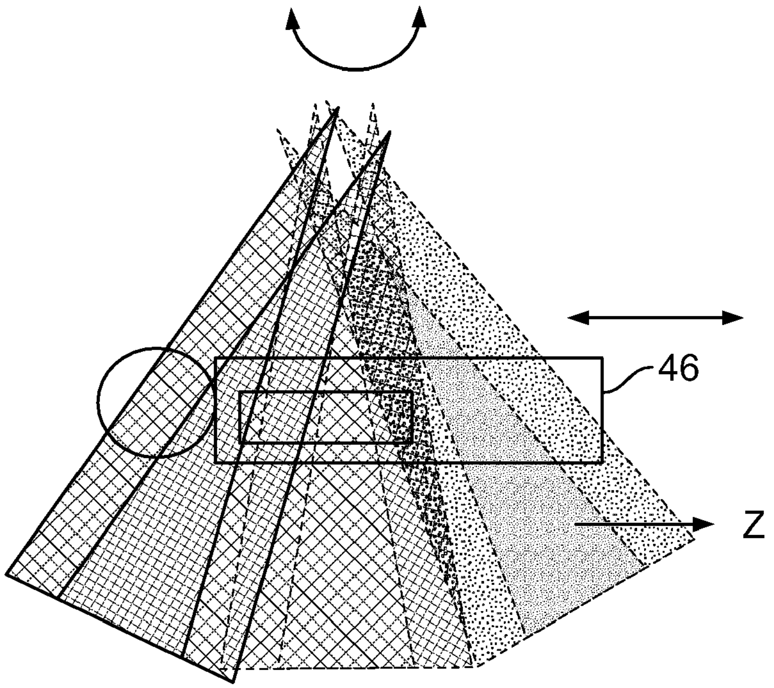
FIG. 9 is a diagram illustrating a pivoting x-ray tube during a tomosynthesis mode of operation in accordance with various embodiments of the invention.

To further enhance the tomosynthesis effect, the x-ray tube 60 can be pivoted as illustrated in FIG. 9 to provide additional angular range during data acquisition. During a scan, the x-ray tube axis is dynamically adjusted while the motorized table 46 translates (represented by the arrow).

It should be noted that in various embodiments, and for example, a seven degree target angle is used to increase the x-ray flux output. With a seven degree target angle, the dimension along the target surface 78 is about eight times longer than the z-dimension. Thus, for a fixed focal spot size in the z-direction, heat can be distributed over a larger track surface to allow higher total x-ray flux.

Figure 10:
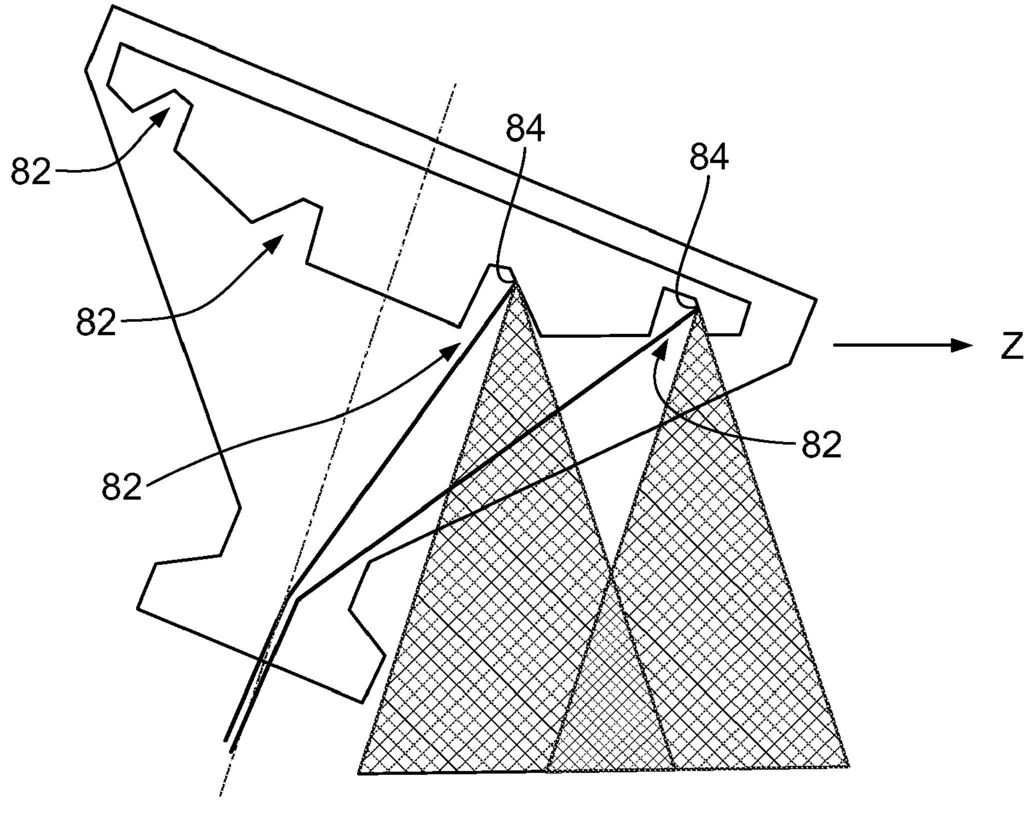
FIG. 10 is a diagram illustrating a target of a focal spot deflected x-ray tube aligned with a z-axis in accordance with other various embodiments of the invention.

Also, it should be noted that with the target surface 78 aligned, and in particular, parallel to the z-axis, the line-focus principle is no longer utilized. As a result, for a given focal spot size in the z-direction, the x-ray flux intensity can be further reduced. To reduce the x-ray flux intensity, one or more grooves 82 or other shaped notches may be provided on the target 70 such that the surface of the electron impacting location is at a small angle relative to the x-ray plane as shown in FIG. 10. For example, one or more angled walls 84 of the grooves 82 are configured in various embodiments to define a target angle relative to the x-ray plane that is less than about ten degrees.

Figure 11:
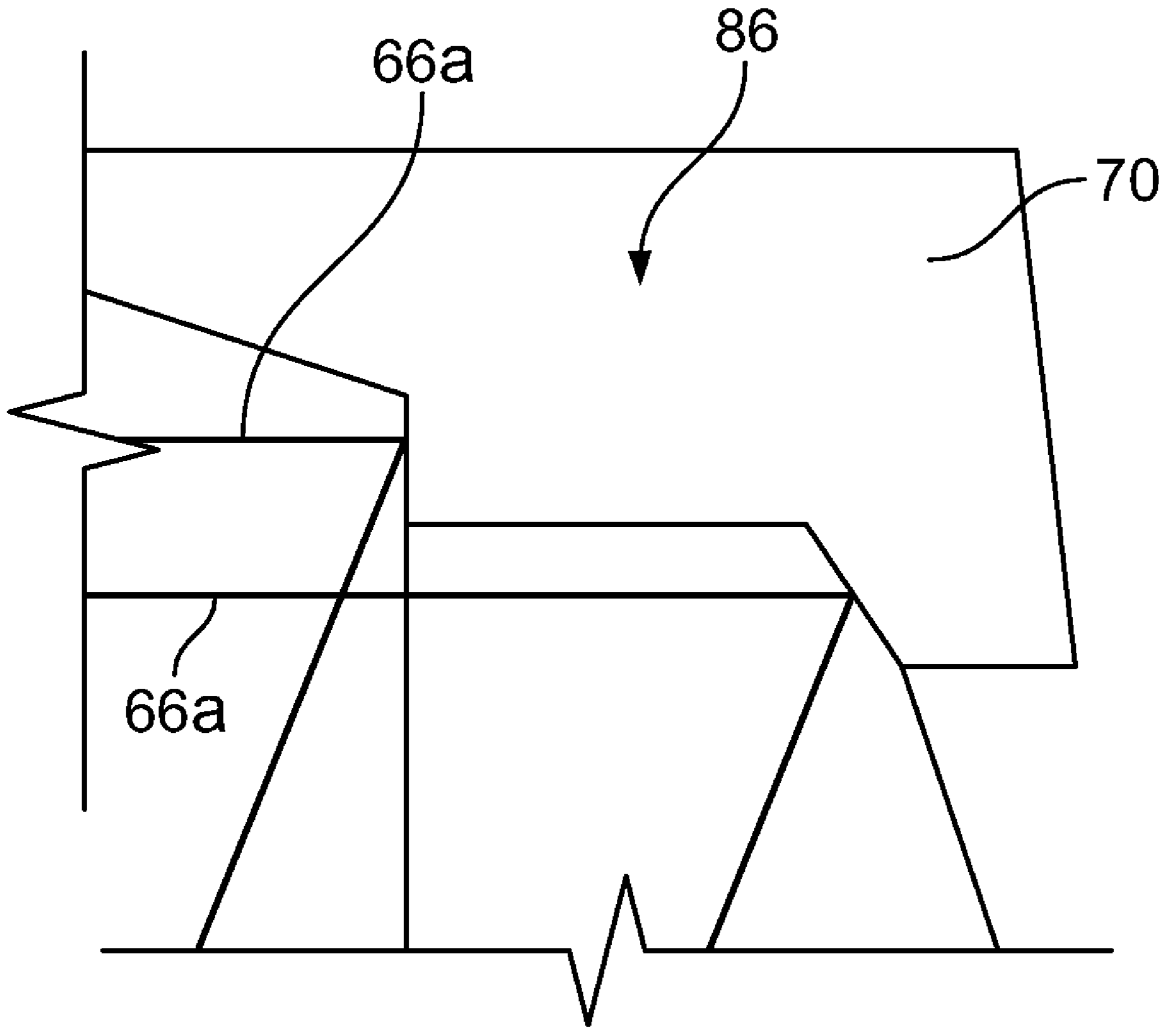
FIG. 11 is a diagram illustrating a target of a focal spot deflected x-ray tube aligned with a z-axis in accordance with other various embodiments of the invention.

It should be noted that the grooves 82 may be modified or replaced with any structure that provides an electron impacting location at a small angle relative to the x-ray plane. For example, as shown in FIG. 11, an angled wall arrangement 86 may be provided having a step-like multiple angled wall configuration. It should be noted that with respect to heat distribution, the angled wall configurations of FIGS. 10 and 11 provide an increased impacting surface area and the line-focus principle is again applied.

Thus, various embodiments provide an x-ray tube that is offset from a z-axis or gantry rotation axis of an imaging system, for example, a CT imaging system. The offset arrangement provides a target of the x-ray tube that is aligned, for example, in parallel relation to the z-axis or gantry rotation axis.

The various embodiments or components, for example, the components of the CT imaging system of controllers or processors therein may be implemented as part of one or more computer systems, which may be separate from or integrated with other systems. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system.

As used herein, the term “computer” may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term “computer”.

The computer system executes a set of instructions that are stored in one or more storage elements, in order to process input data. The storage elements may also store data or other information as desired or needed. The storage element may be in the form of an information source or a physical memory element within the processing machine.

The set of instructions may include various commands that instruct the computer as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms “software” and “firmware” are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray tube comprising:

a cathode configured to emit electrons; and an anode having a target with an angled target surface defining a target angle, the emitted electrons deflected onto the angled target surface, and wherein the angled target surface is substantially aligned with a z-axis parallel to a gantry rotation axis.

2. An x-ray tube in accordance with claim 1 where the emitted electrons are deflected onto a plurality of locations on the target surface.

3. An x-ray tube in accordance with claim 2 wherein the plurality of locations are positioned substantially along the z-axis.

4. An x-ray tube in accordance with claim 2 wherein the plurality of locations are positioned substantially along a target track.

5. An x-ray tube in accordance with claim 2 wherein the plurality of locations are positioned substantially along both a target track and the z-axis.

6. An x-ray tube in accordance with claim 1 wherein the cathode extends along a longitudinal axis that is offset from the z-axis.

7. An x-ray tube in accordance with claim 1 wherein the target surface includes an outer angled portion that is aligned with the z-axis.

8. An x-ray tube in accordance with claim 1 further comprising a housing enclosing the cathode and anode, and wherein the housing is adjustable relative to the z-axis.

9. An x-ray tube in accordance with claim 8 wherein the housing is pivotally adjustable.

10. An x-ray tube in accordance with claim 8 wherein the housing is dynamically adjustable.

11. An x-ray tube in accordance with claim 1 wherein the target surface includes a plurality of grooves extending along the surface.

12. An x-ray tube in accordance with claim 11 wherein the plurality of grooves are spaced apart along the target surface at different focal spots.

13. An x-ray tube in accordance with claim 11 wherein each of the grooves includes at least one angled wall.

14. An x-ray tube in accordance with claim 13 wherein the at least one angled wall is configured to define a target angle relative to an x-ray plane that is less than about ten degrees.

15. An x-ray tube in accordance with claim 1 comprising at least one of an electromagnetic field source and an electrostatic field source configured to deflect the electrons emitted by the cathode.

16. An x-ray tube in accordance with claim 1 wherein the deflected electrons form a plurality of electron beams to produce a plurality of focal spots along the target.

17. An x-ray tube in accordance with claim 1 wherein the angled target surface is configured to increase a spacing between focal spots generated from the electrons emitted from the cathode.

18. An x-ray tube in accordance with claim 1 wherein the target comprises a planar surface offset from the z-axis.

19. An x-ray tube in accordance with claim 18 wherein the cathode is aligned axially with the anode and the target.

20. A computed tomography (CT) system comprising:

a gantry having a gantry opening therethrough defining a z-axis, the gantry configured to rotate about the z-axis; and a radiation source coupled to the gantry, the radiation source utilizing focal spot deflection to project x-rays into the gantry opening and wherein the radiation source is offset from the z-axis.

21. A CT system in accordance with claim 20 wherein the radiation source is adjustably coupled to the gantry.

22. A CT system in accordance with claim 20 wherein the radiation source is dynamically adjustable.

23. A CT system in accordance with claim 20 wherein the radiation source is pivotally rotatable about an axis parallel to the z-axis.

24. A CT system in accordance with claim 20 wherein the radiation source comprises an x-ray tube having a target and wherein the x-ray tube is offset from the z-axis such that a surface of the target is aligned with the z-axis.

25. A CT system in accordance with claim 24 wherein the surface of the target includes a plurality of grooves.

26. A CT system in accordance with claim 20 wherein the gantry is configured to rotate the radiation source in a step-and-shoot mode.

27. A CT system in accordance with claim 20 further comprising a table configured to translate into the gantry opening and wherein the gantry and table remain stationary during data acquisition to generate an x-ray radiography image.

28. A CT system in accordance with claim 20 further comprising a table configured to translate into the gantry opening and wherein the gantry remains stationary and the table translates along the z-axis during data acquisition to generate a tomosynthesis image.

29. A CT system in accordance with claim 20 wherein the radiation source comprises an x-ray tube having a housing and wherein the housing is configured to be adjusted relative to the z-axis during a scan with the gantry remaining stationary.

30. A method for generating x-ray beams with an x-ray tube, the method comprising:

generating a plurality of deflected focal spots along a target of the x-ray tube; and aligning an angled surface of the target with a z-axis along which x-ray beams generated by the deflected focal spots are projected.

* * * * *